US011364343B2

(12) United States Patent
Hung

(10) Patent No.: US 11,364,343 B2
(45) Date of Patent: Jun. 21, 2022

(54) INJECTION DEVICE WITH VELOCITY REGULATOR

(71) Applicant: OWEN MUMFORD LTD, Oxfordshire (GB)

(72) Inventor: Andrew Hung, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 84 days.

(21) Appl. No.: 16/494,338

(22) PCT Filed: Mar. 15, 2018

(86) PCT No.: PCT/GB2018/050659
§ 371 (c)(1),
(2) Date: Sep. 16, 2019

(87) PCT Pub. No.: WO2018/167490
PCT Pub. Date: Sep. 20, 2018

(65) Prior Publication Data
US 2020/0297928 A1 Sep. 24, 2020

(30) Foreign Application Priority Data

Mar. 15, 2017 (GB) .................................. 1704140

(51) Int. Cl.
*A61M 5/20* (2006.01)
*A61M 5/32* (2006.01)
(52) U.S. Cl.
CPC ........ *A61M 5/2033* (2013.01); *A61M 5/3204* (2013.01); *A61M 2005/206* (2013.01); *A61M 2005/2086* (2013.01)
(58) Field of Classification Search
CPC .............. A61M 5/2033; A61M 5/3204; A61M 2005/206; A61M 2005/2086
(Continued)

(56) References Cited

U.S. PATENT DOCUMENTS

| 2,605,766 A | 8/1952 | Uytenbogaart |
| 2013/0102971 A1 | 4/2013 | Olson |
| 2013/0324939 A1* | 12/2013 | Brereton ............... A61M 5/326 604/218 |

FOREIGN PATENT DOCUMENTS

| EP | 2468334 A1 | 6/2012 |
| GB | 2538566 A | 11/2016 |

(Continued)

OTHER PUBLICATIONS

International Preliminary Report on Patentability, dated Sep. 17, 2019, from corresponding PCT application No. PCT/GB2018/050659.

(Continued)

*Primary Examiner* — Bhisma Mehta
*Assistant Examiner* — Nidah Hussain
(74) *Attorney, Agent, or Firm* — Quarles & Brady LLP

(57) ABSTRACT

An autoinjector including a plunger for engaging with the bung, a collar located around the plunger, an insertion spring biasing the collar relative to the rear of the device, and a delivery spring biasing the plunger relative to the collar. The device further includes a stop feature defining the limit of axial movement of the syringe body through the housing, and a collar release mechanism for releasing the collar from the rear of the device to commence insertion and a plunger release mechanism for releasing the plunger from the collar while substantially preventing rearward axial movement of the collar, following insertion, to commence delivery of the medicament. Following release of the plunger from the collar, the plunger is configured to move axially and rotationally relative to the collar, the direction of rotation being changed one or more times with axial movement of the plunger.

9 Claims, 10 Drawing Sheets

(58) Field of Classification Search
USPC .......................................................... 604/218
See application file for complete search history.

(56) References Cited

FOREIGN PATENT DOCUMENTS

| WO | 2005097238 A2 | 10/2005 |
| WO | 2012164389 A2 | 12/2012 |
| WO | 2016189286 A1 | 12/2016 |
| WO | 2017/007850 A1 | 1/2017 |

OTHER PUBLICATIONS

Combined Search and Examination Report issued in UK Patent Application No. GB1704140.1 dated Aug. 15, 2017.
International Search Report, dated Jul. 3, 2018, from corresponding PCT application No. PCT/GB2018/050659.
Written Opinion, dated Jul. 3, 2018, from corresponding PCT application No. PCT/GB2018/050659.
First Office Action from corresponding Chinese Patent Application No. 201880032486.3 dated Mar. 26, 2021 (12 pages) (English translation included).

* cited by examiner

INJECTION DEVICE WITH VELOCITY REGULATOR

CROSS-REFERENCE TO RELATED APPLICATIONS

The present application represents the United States National Stage of International Application No. PCT/GB2018/050659, filed Mar. 15, 2018, which claims priority to British Patent Application Serial No. GB 1704140.1, filed Mar. 15, 2017, and entitled, "INJECTION DEVICE WITH VELOCITY REGULATOR," the contents of which is incorporated herein by reference in their entirety.

TECHNICAL FIELD

This invention relates to injection devices for delivering a dose of medicament from a syringe. In particular, though not necessarily, the invention relates to an autoinjector type device which facilitates powered or power assisted needle insertion and drug delivery.

BACKGROUND

Injection devices are used for the convenient administration of medicaments. For example, injection devices (which may typically be in the form of a pen injector) may be used for providing a single metered dose of a medicament, for example such as Epinephrine in an emergency or for providing regular metered doses of a medicament such as Insulin. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an "autoinjector" device, in which, in addition to automating the delivery of the medicament, the device is also arranged to automate the insertion of a needle into the skin prior to the delivery of the medicament.

Injection devices generally comprise a delivery arrangement which is arranged to automatically deliver a dose from the syringe, and optionally (in the case of an autoinjector) to first displace the syringe within the housing to cause needle penetration. The delivery arrangement generally acts via a plunger which includes or engages a piston (also referred to as a "bung") which is slidably provided within the syringe. In the case of an autoinjector the initial static friction or "stiction" between the bung and syringe resists forward movement of the piston relative to the syringe such that initially the delivery arrangement moves the syringe and piston forward into the needle insertion position. Here, further movement of the syringe is blocked and the delivery arrangement will continue to move forward, overcoming the stiction, and moving the piston and the bung through the syringe.

A common form of delivery arrangement includes an actuation mechanism which biases the plunger forwardly and a trigger mechanism which holds the plunger (directly or indirectly) against the force of the actuation mechanism until the trigger is released. For example the actuation mechanism may comprise a drive spring (for example a compression spring) which is held in an energised (or primed) position prior to release by the trigger.

An injection device of the autoinjector type is described in WO2016/189286. The actuation mechanism of this device comprises two springs, a first, relatively weak, insertion spring for moving the syringe through the device housing to insert the needle into the skin and a second, relatively strong, delivery spring for driving the plunger and piston through the syringe body.

WO2016/189286 addresses a known problem with autoinjectors, namely that the force exerted by the insertion spring during the needle insertion phase may be great enough to damage the syringe when it bottoms out against the housing at the end of its travel. The problem is mitigated by incorporating a velocity regulator which limits the velocity of the syringe until it has bottomed out.

SUMMARY

According to the present invention there is provided an injection device for delivering a medicament from a syringe contained, in use, within a housing of the device, the device being configured to move the syringe through the housing to cause insertion of a needle of the syringe into a user's skin and to subsequently move a bung of the syringe through a syringe body to deliver medicament through the needle. The device comprises a plunger for engaging with said bung, a collar located around the plunger, an insertion spring biasing the collar relative to the rear of the device, and a delivery spring biasing the plunger relative to the collar.

The device further comprises a stop feature defining the limit of axial movement of the syringe body through the housing, and a collar release mechanism for releasing the collar from the rear of the device to commence insertion and a plunger release mechanism for releasing the plunger from the collar while substantially preventing rearward axial movement of the collar, following insertion, to commence delivery of the medicament. Following release of the plunger from the collar, the plunger is configured to move axially and rotationally relative to the collar, the direction of rotation being changed one or more times with axial movement of the plunger.

Optionally, one of said plunger and said collar defines a track and the other comprises a track follower for engaging said track to thereby define the axial and rotational movement of the plunger within the collar.

Optionally, said track follower comprises a projection extending radially outwardly from said plunger and said track is formed through, or on an inner surface of, said collar.

Optionally, said track comprises two or more sequential and alternately inclined track sections.

Optionally, said track comprises a linear track section, subsequent to the inclined sections, which follows only a linear, axial direction.

Optionally, the device is configured such that the track follower enters the linear section of the track after the plunger has engaged with the bung.

Optionally, said plunger release mechanism comprises a latching mechanism for latching the collar relative to the housing upon or immediately prior to releasing the plunger from the collar.

Optionally, the insertion spring and the delivery spring are the same spring.

Optionally, the injection device further comprises a syringe.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

In the following embodiments, the terms "forward" and "front" refer to the patient facing end of the injection device or component thereof. In other words, the front end of the injection device is the end proximal to the injection site during use. Likewise, the term "rear" refers to the non-patient end of the injection device assembly or component thereof. In other words, the term "rear" means distant or remote from the injection site during use.

Axial, radial and circumferential are used herein to conveniently refer to the general directions relative to the longitudinal direction of the injection device (or components thereof). The skilled person will, however, appreciated that these terms are not intended to be narrowly interpreted (and for example the injection device may have a non-circular and/or irregular form). Typically, regardless of the chosen injection device external profile the syringe or cartridge will have a conventional, generally cylindrical, elongate form and will include or be associated with a needle extending longitudinally from a forward end thereof. Thus, the longitudinal axis of the injection device will typically substantially coincide with (or be parallel to) the axial direction of the syringe or cartridge.

Figure 1:
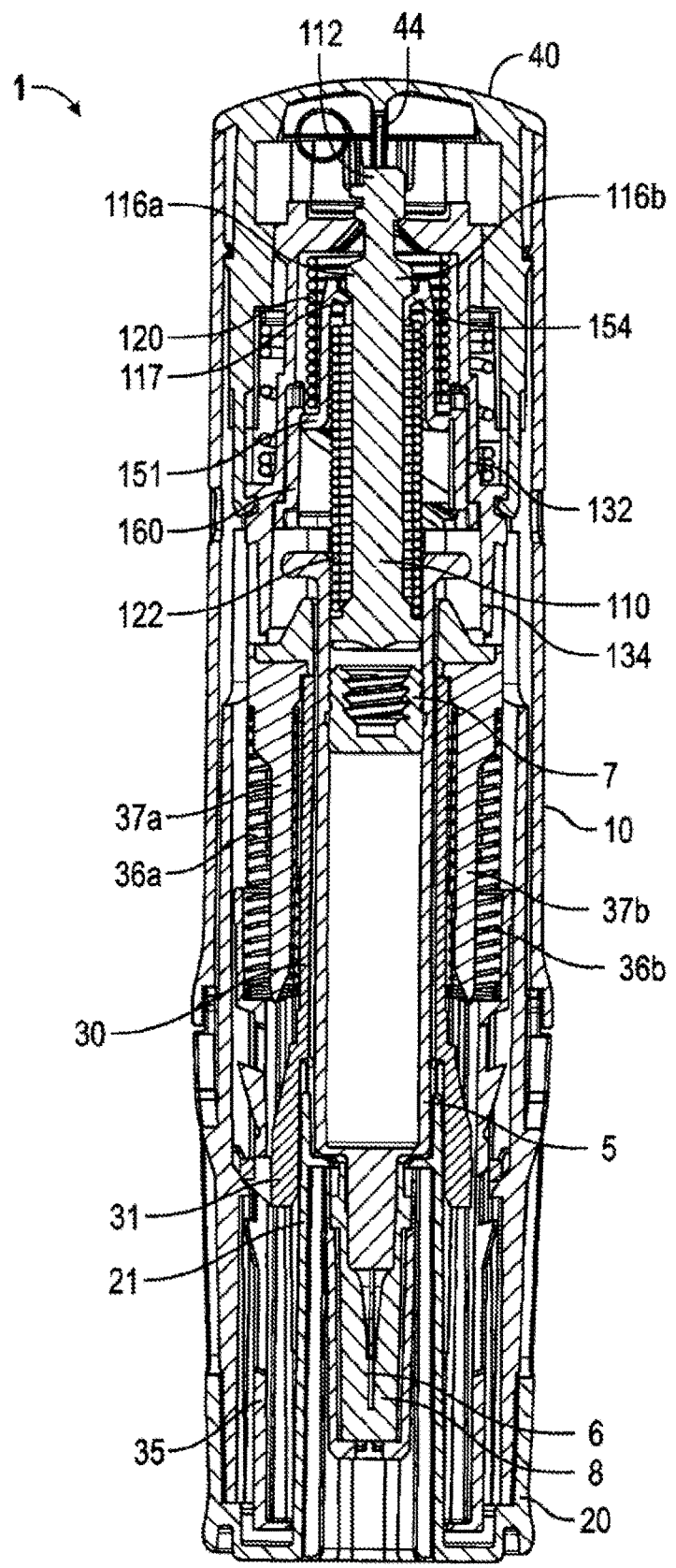
FIG. 1 is a cross-sectional view of a prior art autoinjector.

FIG. 1 shows a cross-sectional view of a prior art autoinjector 1 as disclosed in WO2016/189286. The autoinjector comprises a housing 10 within which is provided a syringe 5 of medicament. The housing 10 has a generally elongate tubular shape with a generally oval cross-sectional profile (and has a longitudinal axis running through the centre of the syringe).

The syringe 5 is a conventional syringe having a bung 7 within its body and a needle 6 at its forward end which may be initially protected (so as to remain sterile) by a removable needle shield or "boot" 8. The illustrated autoinjector 1 is generally intended to be a single use device and, therefore, the view of FIG. 1 may typically represent a fully assembled, ready to use device as provided to an end user. A cap 20 is provided which closes the forward end of the autoinjector 1 prior to use. The cap 20 includes an internal formation, comprising rearwardly extending members 21, arranged to engage the removable needle shield 8 of the syringe 5 such that removal of the cap 20 from the housing 10 during use also removes the removable needle shield 8 from the syringe 5.

The autoinjector 1 comprises a forward subassembly in a forward portion of the housing 10 and a rearward assembly in a rearward portion of the housing 10. The two housing portions may be snap fit together, about the syringe, during assembly. The forward subassembly comprises the components which surround and/or are initially forward of the syringe 5. The rearward subassembly comprises those components which are initially rearward of the syringe 5.

A forward portion of the housing 10 contains a syringe carrier 30 for movably mounting the syringe within the housing 10 to enable automatic needle penetration. It is noted that prior to the removal of the cap 20, the rearwardly extending members 21 of the cap 20 underlie spring fingers 31 of the syringe carrier 30. This arrangement thus prevents inward movement of the spring fingers 31 prior to removal of the cap 20 and, therefore, blocks unlatching of the syringe carrier 30 and prevents movement relative to the housing 20.

A needle shroud 35 is also provided and arranged to shroud the needle after use (when the syringe 5 and syringe carrier 30 are in a forward position) to prevent needle stick injuries. The shroud 35 is activated by a pair of side-by-side shroud springs 36a, 36b carried on respective spring guides 37a, 37b. Operation of the shroud 30 and carrier 35 is not described here in any detail. However, it is noted that the arrangement may substantially correspond to the arrangement described in WO2012/085580. Other arrangements are possible however and the methods and apparatus disclosed herein may be used in such other arrangements. For example, the shroud may be deployed by a single spring (or other biasing means) and the single spring may be the same spring used to drive the plunger into the syringe barrel to deliver a substance therefrom.

A rearward portion of the housing 10 includes a trigger button 40 which is inserted into the rearward portion of the housing 10 from the rearward end so as to substantially close the rearward end of the housing 10. The trigger button 40 has a cup-like profile with side walls which are arranged to fit within (and be substantially concentric with) the rearward housing 30 and an end wall which closes the rear end of the housing. The trigger button 40 includes a pair of forwardly extending resilient arms 41a and 41b which are arranged to provide an engagement between the trigger button 40 and the injector 1.

Figure 2:
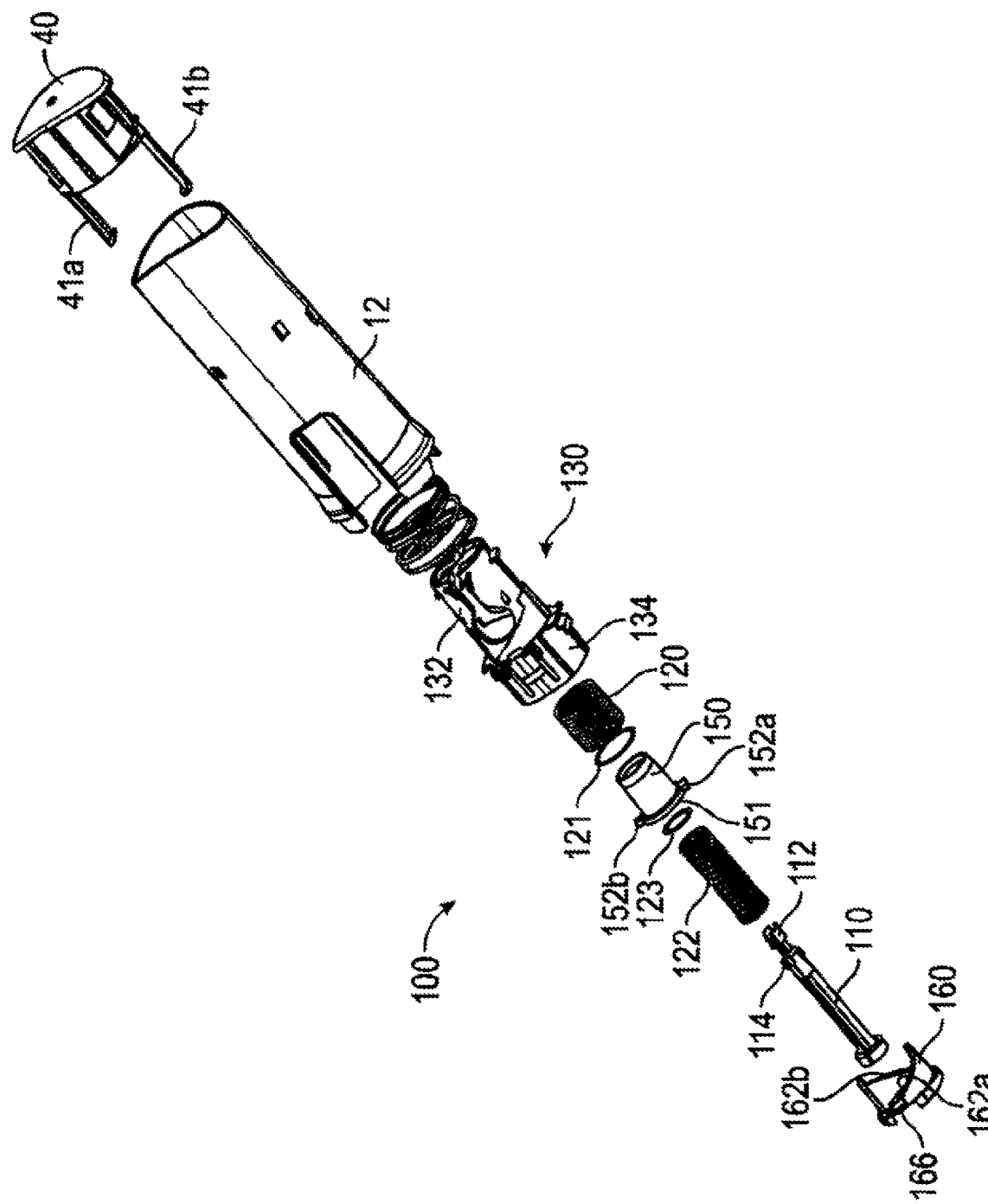
FIG. 2 is an exploded view of a rear section of the autoinjector of FIG. 1.

The rearward portion of the housing 10 also includes a drive mechanism 100, best seen in FIG. 2. The drive mechanism 100 includes a plunger 110 which is arranged to engage the bung 7 of the syringe 5 in use. The plunger 110 is driven forwards in use by a pair of concentric drive springs 120 (insertion spring) and 122 (delivery spring), although it will be appreciated that in other embodiments a single spring may be used. An intermediate drive member in the form of a collar 150 (which also functions as part of the velocity regulator as described below) is provided between the first 120 and second 122 drive springs. A pair of thrust washers 121, 123 are provided respectively between the first 120 and second 122 springs and the drive member/collar 150. A latch 130 is arranged concentrically around the drive springs 120, 122, intermediate member/collar 150 and plunger 110. The latch 130 is arranged to hold the plunger 110 against the bias of the springs 120, 122 until the latch is released via the trigger button 40. The latch 130 comprises a rear body portion 132 having a split cylinder profile and defining a latch aperture at its rear end and a forward connecting body portion 134. The basic functional operation of the drive mechanism 100 may substantially as described, for example, in WO2012/049484 and WO2015/011488, although other arrangements are possible without departing from the scope of the claimed invention.

An exemplary actuation mechanism will now be described in further detail with particular reference to FIGS. 2 and 3 to 6.

FIG. 2 shows an exploded view of a rearward subassembly of the autoinjector device 1 (in which it may be noted that the housing 10 includes a discreet rearward housing component 12). In FIG. 3A the housing is omitted for clarity and in FIGS. 3B and 3C only the components directly associated with the velocity regulator are shown for further clarity. As noted above, the actuation mechanism includes a latch member 130 which is removably fixed into the housing 10 (by a snap fit arrangement) and initially retains the plunger 110 against the forward biasing force of the actuation springs 120 and 122 (which act via the intermediate member 150). At the rear of the injection device 1 is provided a trigger button 40 which is initially retained in position by the pair of arms 41a, 41b. In a central portion of the inner surface of the rearward face of the button 40, a forwardly extending boss 44 is provided which acts to urge the plunger 110 out of engagement with the latch member 130 during activation (in a manner such as that described in the applicants earlier patent applications referred to above).

The boss 44 comprises an arrangement which is in splined engagement with the rearward head 112 of the plunger 110. It will be seen that the rearward end of the plunger 110 is provided with a pair of axially extending radial slots which extend forwardly from the head 112 and the boss 44 comprising a corresponding pair of projections. As will be explained in further detail below, this arrangement ensures that the plunger 110 is rotationally fixed relative to the trigger button 40. In turn the trigger button 40 is non-rotationally engaged with the housing 10 (for example, due to the non-circular shape of the housing 10 and trigger button 40 and/or the engagement between the legs 41a, 41b of the trigger button 40 and the latch 130).

The actuation mechanism 100 of the autoinjector device 1 also includes a velocity regulator arranged to control or limit the initial velocity of the plunger 110 upon release of the actuation mechanism. The velocity regulator utilises a cam member 152 which travels along a cam surface 162 which provides an inclined plane along which the cam member 152 will travel during actuation.

The cam surface 162 is conveniently provided on a cam body 160 which is engaged with the forward portion 134 of the latch 130 by a snap-fit arrangement including, for example, at least one latch member 166. To ensure proper alignment between the cam body 160 and the latch member 130, an alignment flange 167 may also be provided on the cam body 160 to abut a corresponding shoulder 135 in the latch 130. The cam body 160 may comprise a generally annular body with an external profile which matches the required internal profile of the latch 130. A pair of helical cam surfaces 162a, 162b are defined at the rearward end of the cam body and are forwardly sloped to define a pair of parallel cam paths which extend circumferentially around the interior of the injection device 1 whilst also being inclined forwardly in the manner of a partial screw thread. A correspondingly profiled shoulder may be provided rearwardly of the cam surface 162 on the interior surface of the latch 130 such that when the cam body is assembled with the latch 130, a slot or track 138 is defined (and configured to receive the cam members 152). Each cam surface 162 is provided with stop 163 at its rearward end (which acts to separate the separate cam paths defined by the cam body 160) and ends with a cut-out or aperture 164 at the forward-most end of the cam surface 162.

Figure 3:
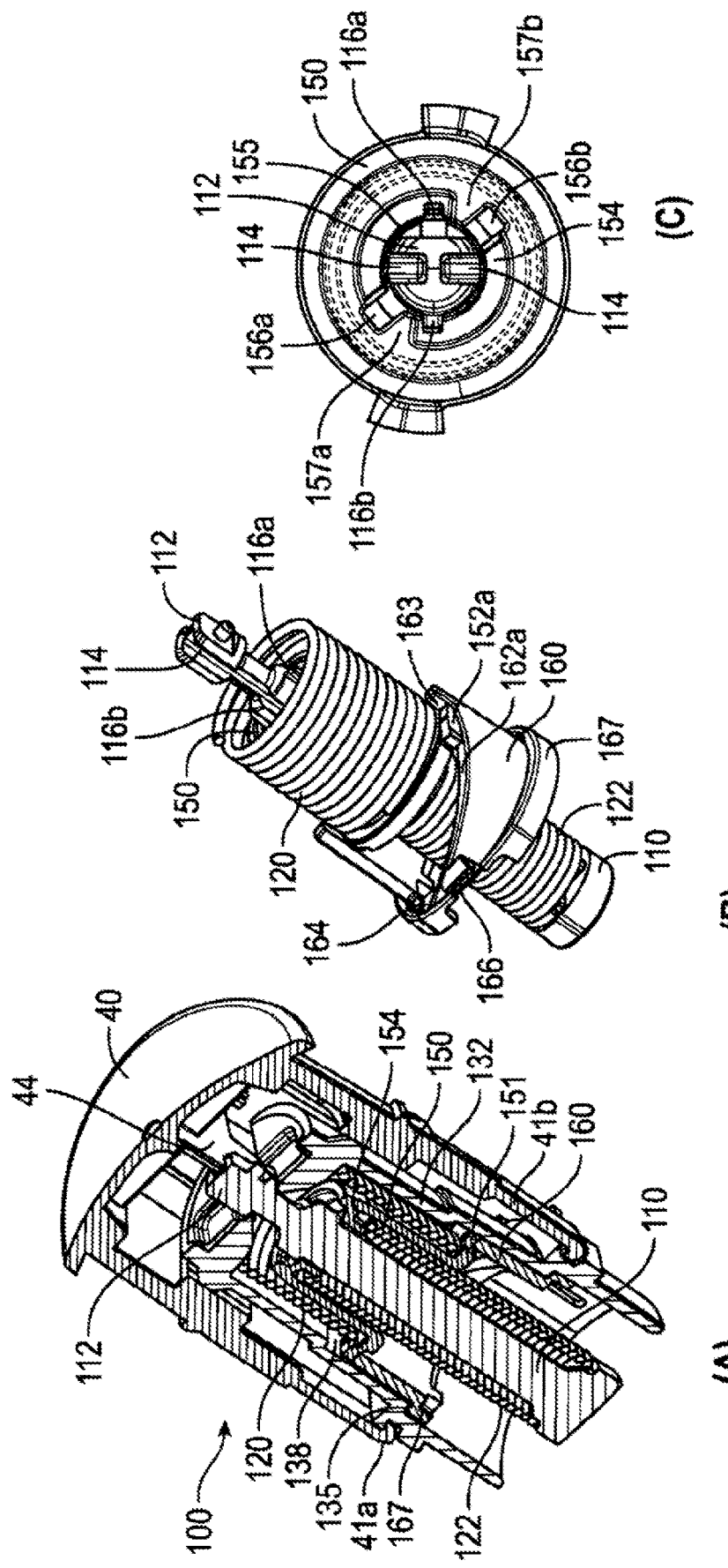
FIG. 3 is a cross-sectional view and partial end view of an actuation mechanism including a velocity regulator of the autoinjector of FIG. 1, in a pre-fired state.
Figure 4:
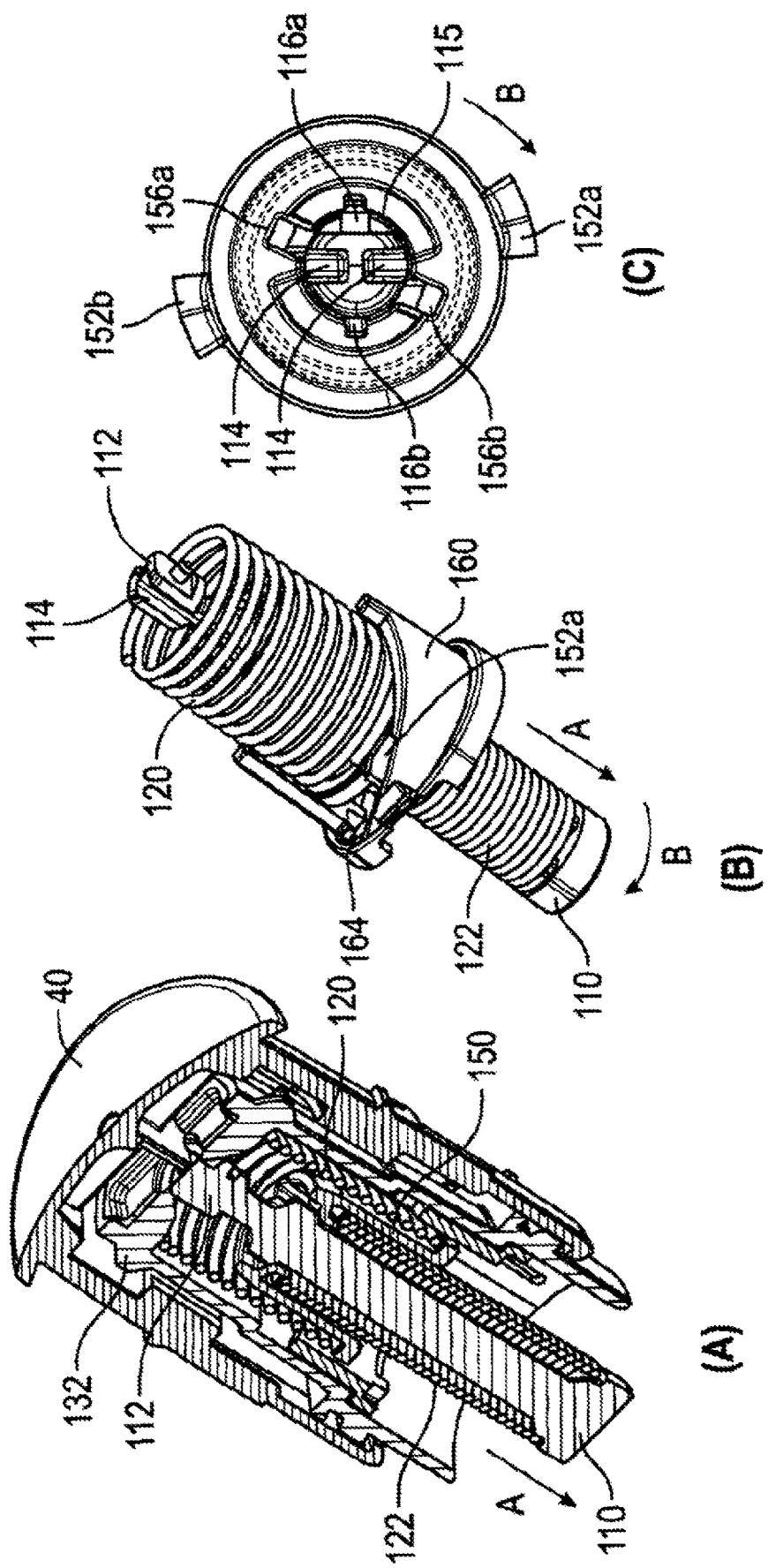
FIGS. 4 to 6 are sequential views corresponding to FIG. 3 during the activation of the autoinjector of FIG. 1.

The collar 150 acts as an intermediate drive member between the first compression spring 120 and second compression spring 122. Accordingly, the collar 150 includes an external radial flange 151 at its forward end which provides a seat for the first compression spring 120 and an internal radial flange 154 at its rearward end which provides a seat for the second compression spring 122. The thrust washers 121, 123 are disposed on the seats between the radial flanges 151, 154 of the collar and the springs 120, 122. The collar 150 is a generally cylindrical body and is provided with a pair of radially opposed outwardly extending lugs 152a, 152b. The lugs 152a, 152b are provided on a radially outer surface of the outwardly extending flange 151 (such that they do not impede either of the compression springs 120, 122). The internal flange 154 at the rear of the collar 150 includes an aperture 155 through which the head 112 of the plunger extends when the actuation mechanism 100 is in the pre-fired (or primed) condition as shown in FIG. 3.

The aperture 155 is provided with a keyed profile defined by a cylindrical central aperture portion 155a and a pair of opposed radial slots 156. The cylindrical side walls of the collar 150 extend rearwardly, slightly beyond the flange 154 so as to define a cylindrical cup which surrounds the flange 154 and the aperture 155. Inwardly radially extending stop members 157a, 157b may be provided adjacent to one side of the radial slots 156a and 156b.

A rearward portion of the plunger 110 which is axially rearward of the aperture 155 in the pre-fired configuration is provided with a profiled cross-section for engagement with the keyway defined by the aperture 155. This profiled portion is immediately forward of the head 112 of the plunger which is configured to be engaged by the latch 130. The profiled portion is defined by a pair of radially outwardly extending projections 116a, 116b which provide a forward facing shoulder 117 is initially engaged with the rearward face of the flange 154. The radial projections 116a, 116b are configured such that they may pass through the radial slots 156a, 156b when the slots 156 and projections 116 are aligned.

The actuation sequence of the mechanism 100 and velocity regulator will now be described with reference to FIGS. 3 to 6. The pre-firing configuration of the actuation mechanism 100 is shown in FIG. 3. In this configuration the head 112 of the plunger 110 is retained in the aperture of the latch 130. As such both the first compression spring 120 and the second compression spring 122 are in a compressed, energised, state. The trigger button 40 is in splined engagement with the rearward end of the plunger 110 via the boss 44 being positioned within the slots 114 at the rear of the plunger 110. The rearward portion 132 of the latch 130 is unable to expand to release the head 112 of the plunger 110 as part of the trigger button abuts an outer surface of the rearward section of the latch 132.

In this position the radial projection 116 of the plunger 110 is rearwardly positioned relative to the aperture 155 of the collar 150 and the relative rotational position of the plunger 110 and the collar 150 has been set during assembly such that the projections 116 are misaligned with the slots 116 and, in fact, it will be noted that the projections 156 abut against the stops 157 of the collar 150. In this initial position the cam members 152 are positioned at a rearward end of the cam surfaces 162 and essentially abut against the stops 163 at the rearwardmost end of the cam surfaces 162.

In order to activate the device the user urges the trigger button 40 forwardly relative to the housing 10 of the autoinjector device 1 (having firstly carried out any required initiation steps such as removal of the cap from the forward end of the autoinjector device 1 and/or releasing any safety mechanisms, such as an interlock). The forward movement of the trigger button 40 moves the blocking arrangement of the cap 40 out of alignment with the rearward section 132 of the latch 130 and may also directly transmit a forward force onto the rear of the plunger 110 via the engagement of the boss 44 with the head 112 of the plunger 110. As the result of this trigger action, the head 112 of the plunger 110 is released from the trigger 130 freeing the rearward spring 120 to urge the plunger forwardly, in the direction of arrow A, via the outer flange 151 or the collar 150.

This forward movement causes the cam members 152a, 152b to travel along the inclined path of the cam surface 162a, 162b. As the first spring 120 expands its axial force is transmitted by the collar 150 through the fully compressed second compression spring 122 to the forward end of the plunger 110. However, initially the plunger 110 is unable to travel beyond the collar 150 as the radial projections 116 engage the internal flange 154 at the rear of the collar 150.

Due to the splined engagement between the trigger button 40 and the plunger 110 the collar 150 must rotate relative to the plunger 110, in the direction of the arrow B, as the cam members 152a, 152b travel along the cam surfaces 162a, 162b. The thrust washers 121, 122 prevent or reduce any frictional resistance to the rotation of the collar 150 by the springs 121, 122. As best seen in the end view of FIG. 4C, the resulting relative rotation of the collar 150 causes the aperture 155 to rotate relative to the radial projections 116a, 116b moving the projections off the stop surface 157 and towards the radial slots 156a, 156b.

Figure 5:
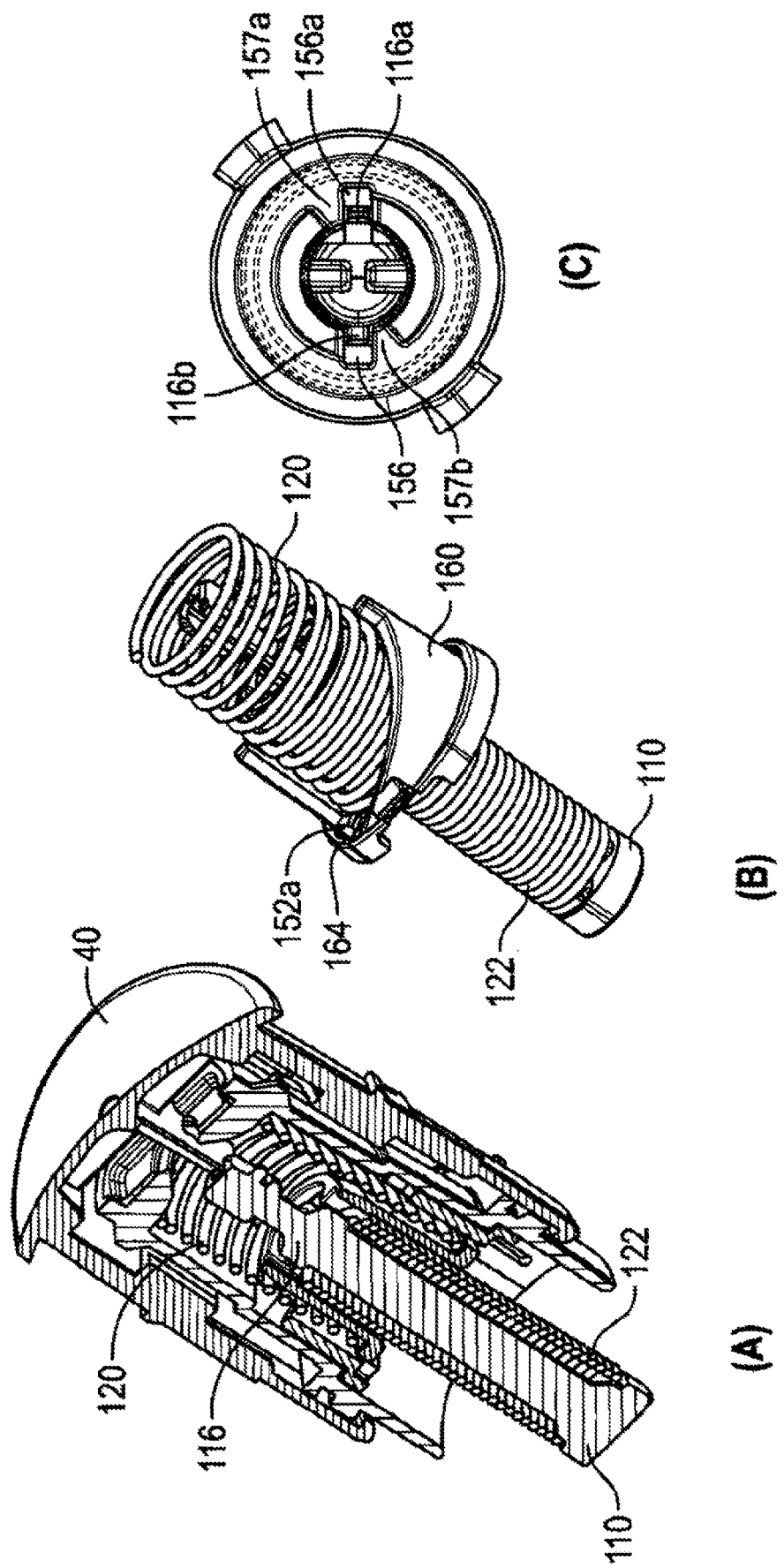

As the plunger 110 and collar 150 continue to move forwardly, the collar 150 reaches its fully rotated position as shown in FIG. 5. In the illustrated example the fully rotated position corresponds to approximately one half turn of the collar 150 (although the skilled person will appreciate that the particular configuration may vary depending on the profile of the cam surface and the required sequencing of the actuation mechanism 100). In this position the radial slots 156a, 156b have rotated into alignment with the radial projections 116a, 116b and the cam members 152a, 152b have also reached the end of the cam surface 162a, 162b and have moved into alignment with the cut-out/aperture 164 at the end of the cam path.

Figure 6:
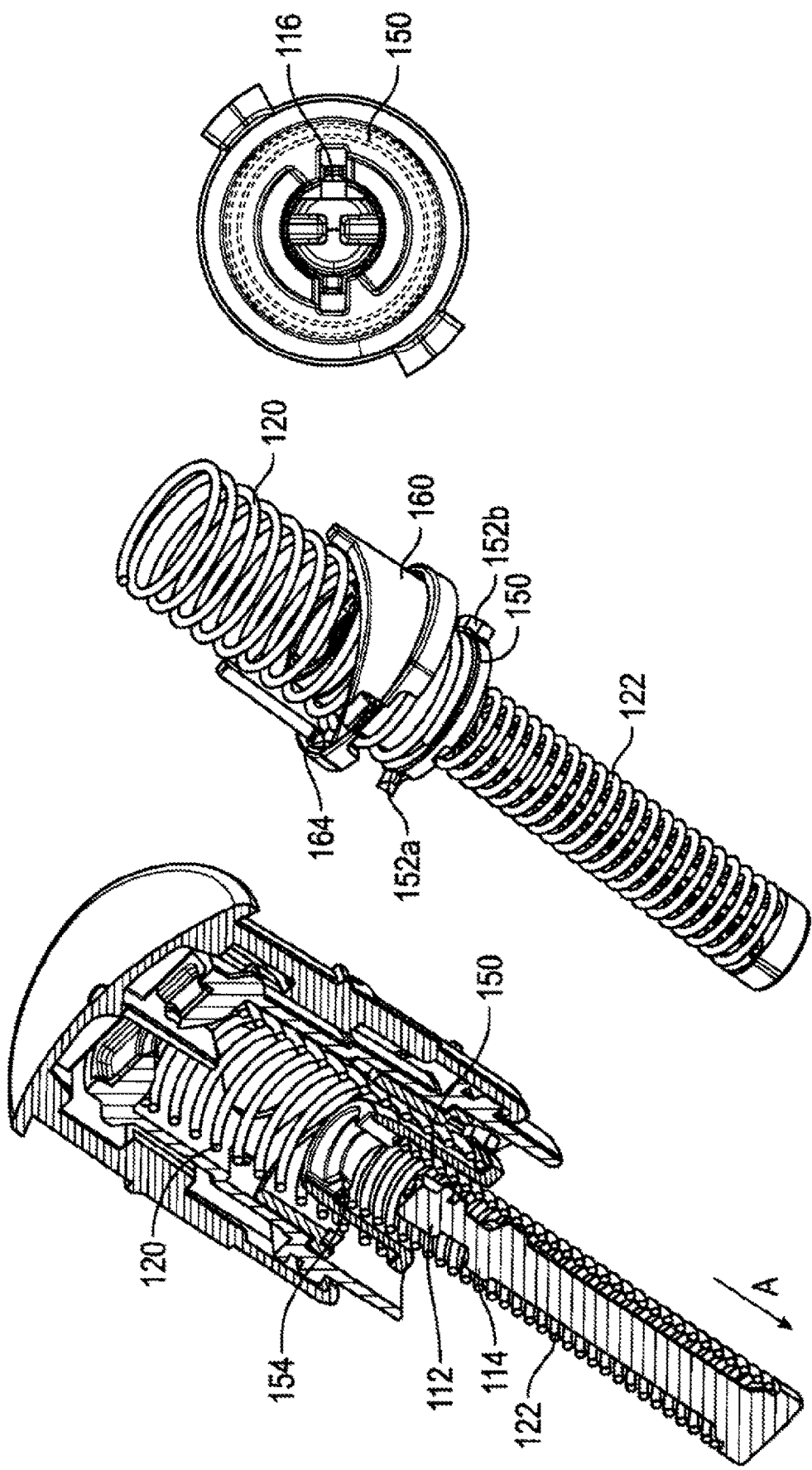

Accordingly, as shown in FIG. 6, the velocity regulator may now disengage so as to allow the plunger to continue freely forward (continuing in the direction of arrow A). In this forward movement the plunger 110 moves forward relative to the collar 150 due to the radial projections 116a, 116b passing through the radial slots 156a, 156b and the collar 150 is also allowed to pass forwardly of the cam body 160 due to the cam members 152a, 152b passing through the cut-outs 164. In other words, both the collar 150 and plunger 110 are disengaged and the collar 150 and cam body 160 are disengaged. In the illustrated embodiment the disengagements both occur substantially simultaneously (although the skilled person will appreciate that this may depend on the particular sequencing required). Once the radial projections 116a, 116b have passed through the radial slots 156a, 156b, the second drive spring 122 is free to expand and push against the collar 150 and plunger 110. The collar 150 is also free from the velocity regulator, and the first drive spring 120 and second drive spring 122 act on the plunger.

Once the velocity regulator is disengaged, the forward motion of the plunger 110 is no longer regulated (but the skilled person will appreciate that the plunger may now be pressing against the medicament within the syringe 5 such that its motion is naturally damped). The forces exerted by the springs 120, 122 on the plunger and the collar are dependent on the relative strengths of the first spring 120 and second spring 122, as well as the damping force provided by the medicament through the plunger 110. The axial motion of the collar 150 once the collar 150 has passed through the velocity regulator is therefore application-dependent.

Although the device has been described above with reference to one embodiment, it will be appreciated that various changes or modifications may be made. For example, the skilled person will appreciate that the timing of the disengagement between the components of the velocity regulator may depend on the particular configuration of the device. For example, the velocity regulator may be intended to slow/control the movement of the plunger 110 only during an initial movement in which the plunger 110 is brought into contact with the bung 7 of the syringe 5 (since manufacturing tolerances will usually make it necessary for the forward end of the plunger 110 to be initially spaced from the rearward end of the bung 7) so as to reduce impact thereto. Alternatively, or additionally, the velocity regulator may be configured to control the speed of movement of the actuation mechanism until the needle insertion step of the actuation process has been completed. Whilst the illustrated example includes two opposing counter-surfaces the skilled person will appreciate that more or less features may be utilised.

In the illustrated device the cam surface defines a substantially constant helical cam path but the skilled person will appreciate that the surface may have other sloped profiles (for example, a variable angle of incline) depending upon the velocity profile required for the forward movement of the plunger 110. Whilst an arrangement having two compression springs is advantageous in providing a compact actuation mechanism the skilled person will appreciate that in some embodiments only a single compression may be utilised. For example, in a single spring arrangement, the cam members could be formed on a portion of the plunger and the plunger may be allowed to rotate relative to the housing.

Autoinjectors must be capable of operating correctly substantially independently of the fill level or syringes. In some cases where the fill level is low the bung will be relatively far down inside the syringe body whilst, conversely, where the fill level is relatively high the bung will be close to the top of the syringe body. When the device is assembled around the syringe therefore, the gap between the plunger head and the bung will be unpredictable. When the delivery spring is released at the point where the syringe bottoms out at the end of the insertion phase, the force exerted on the plunger will be very high but the resistance presented to the plunger will be low until the bung is contacted. The resulting high velocity of the plunger can be problematic. It is desirable to incorporate into the device some means to regulate the velocity of the plunger following release of the delivery spring up to the point at which the plunger head contacts the bung. In a single spring embodiment, the means to regulate the velocity of the plunger may regulate velocity during a phase in which the plunger approaches the bung and/or during a delivery phase when the medicament is delivered from the syringe.

A modified autoinjector will now be described. Only relevant parts of the autoinjector will be described and the skilled person should refer to the previously described exemplary arrangement or other known arrangements to understand the structure and function of other components of the device.

Figure 7:
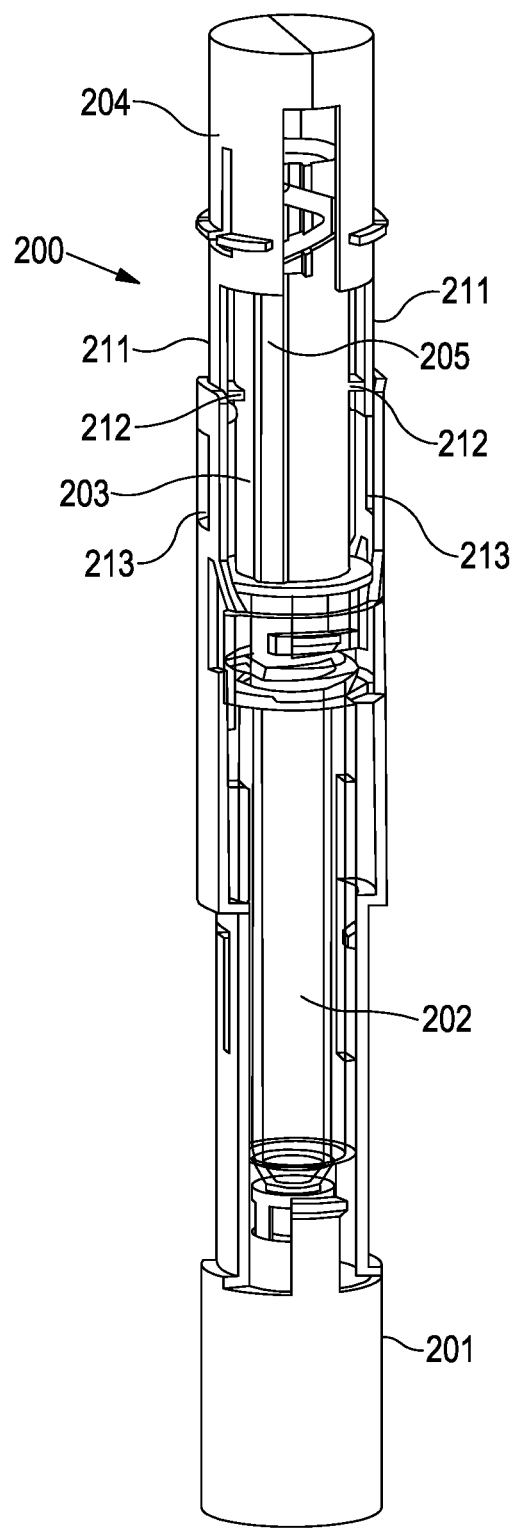
FIG. 7 is a perspective and partial cross-sectional view of an autoinjector according to an embodiment of the present invention.
Figure 8:
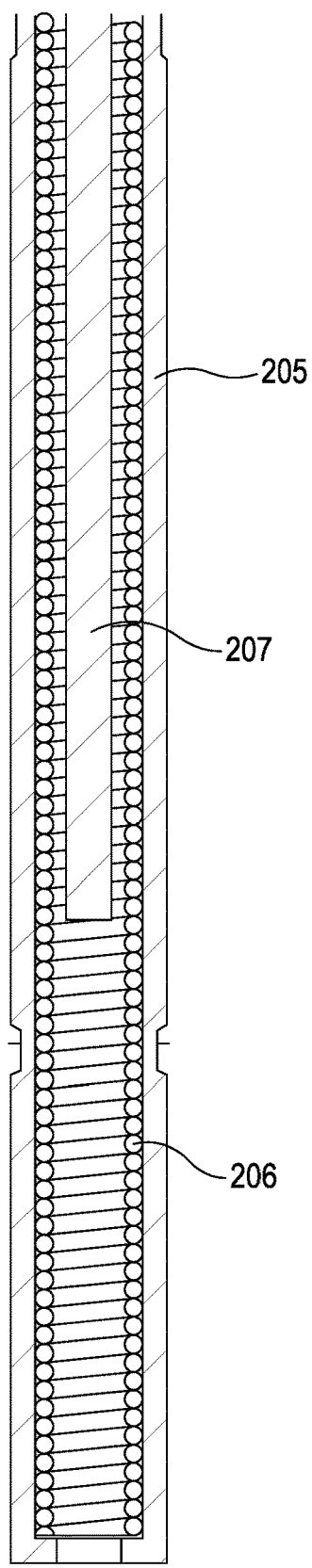
FIG. 8 is a cross-sectional view of a plunger component of the autoinjector of FIG. 7.

FIG. 7 illustrates in partial cross-section certain components of an injection device or autoinjector 200. For the sake of clarity various components are omitted, e.g. the insertion and delivery springs, the bung and needle of the syringe body, the outer housing etc. FIG. 7 shows only a needle shroud and lock-out shroud 201 having a generally cylindrical construction, a syringe body 202, an elongate collar 203, a cap 204, and a plunger 205 mounted coaxially within the collar 203. Again, although not shown, an insertion spring is provided in order to urge the plunger 205 and collar 203 forwards, the top of the insertion spring acting against the cap 204 which is essentially fixed relative to the housing. A delivery spring 206 is provided around a central pillar 207 inside the plunger 205, best seen in the cross-section view of the plunger shown in FIG. 8. The delivery spring biases the plunger 205 against the collar 203. As explained previously, this arrangement is only exemplary and, as would be understood by the skilled person, a single spring arrangement is also possible in which a single spring is used to insert the needle to the injection device and also to drive the plunger into the barrel to deliver the medicament.

Figure 9:
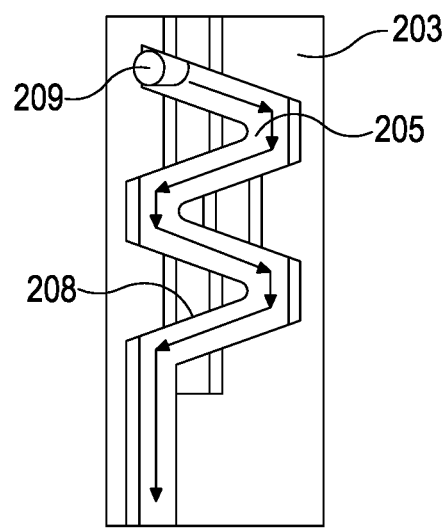
FIG. 9 illustrates portions of a sleeve and collar of the autoinjector of FIG. 7.
Figure 10:
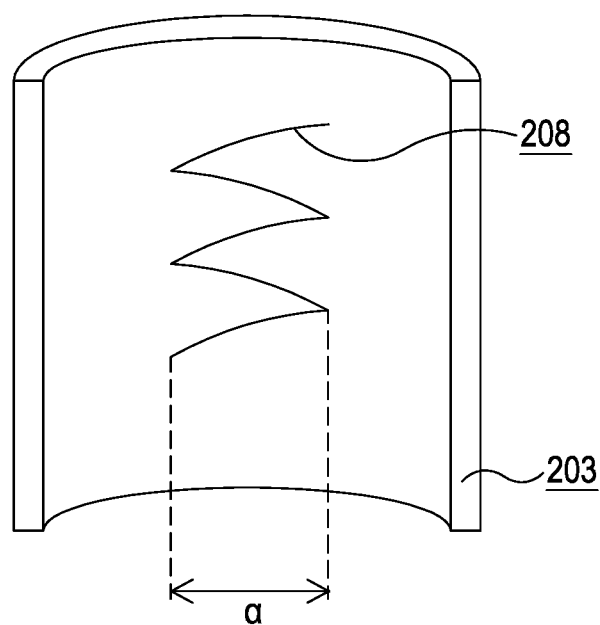
FIG. 10 illustrates a partial cross-section through the collar of FIG. 9.

FIG. 9 shows a detail of the device 200 of FIG. 7. In particular, it shows a guide track or cam surface 208 extending along the collar 203. The track 208 initially follows a zig-zag path prior to following a linear path. The linear path is, in this case, substantially axial with respect to the device. This track 208 may be formed as a cut-through the wall of the collar 203 or may be formed as a recess in the inner surface of the collar 203. FIG. 9 also shows a cylindrical projection 209 extending outwardly from the outer surface of the plunger 205. The projection 209 is engaged with the track 208 and hence restricts the relative motion of the collar 203 and the plunger 205. FIG. 10 illustrates the path of the track by way of a cross-section through the collar 203.

As will be apparent from FIG. 7, the cap 204 comprises a pair of depending, flexible legs 211 which are initially prevented from flexing outwardly by engagement with an upper part of the shroud 201. Each upper part has respective inwardly extending feet 212 which pass through slots in the collar 203 to engage and lock the axial position of the collar 203 at the rear of the injection device 200, against the biasing force of the insertion spring.

Figure 11:
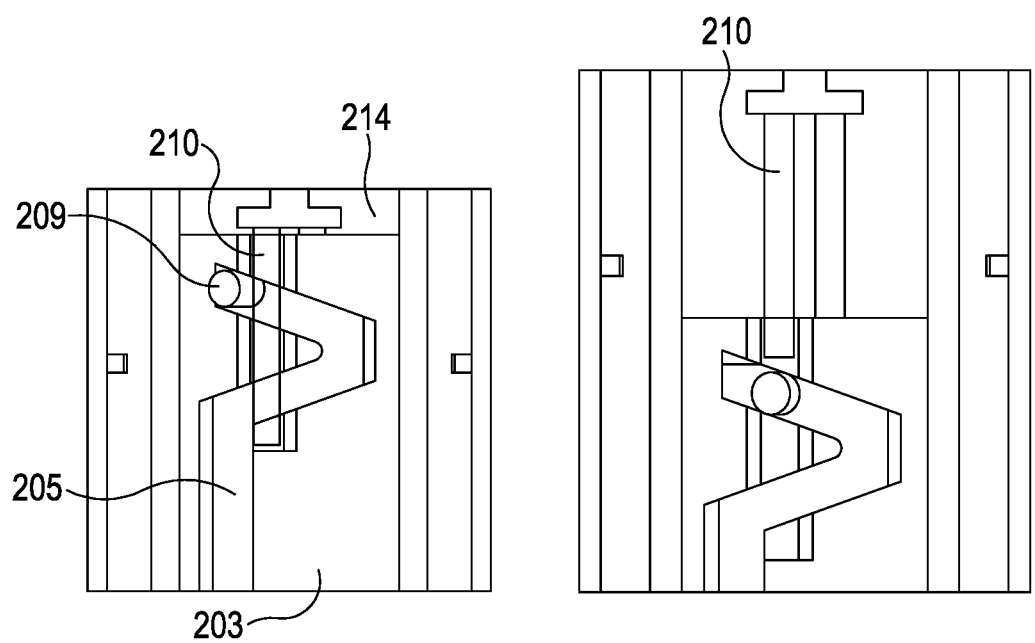
FIG. 11 illustrates a detail of the autoinjector of FIG. 7 in two operating states.

As shown in FIG. 11, an inwardly extending rib 210 is provided on an inside surface of the body 214 and projects through a slot formed in the cap 204. Since the delivery spring 206 provides a relative axial force between the collar 203 and plunger 205, the spring urges the projection 209 to rotate down the track 208. However the rib 210 prevents the projection 209 from rotating until the plunger 205 and collar 203 have reached or almost reached an insertion position.

To activate the device the user grasps the outer housing and presses the end of the shroud 201 against the skin. This action pushes the shroud 201 into the housing, causing a pair of release windows 213 to move up over the flexible legs 211. When these are aligned, the legs 211 pop out through the windows 213, releasing the collar 203 from cap 204. The insertion spring now acts to move the collar 203 (and therefore also the plunger 205) forwards through the injection device 200. In a single spring device, the delivery spring would do this as well as driving the plunger into the barrel of the syringe. The collar 203 makes contact with the syringe body 202 and moves the syringe body 202 forwards. The syringe body 202 and collar 203 move forwards until the syringe body 202 reaches an injection position. A stop at the injection position prevents further movement of the syringe body 202 and collar 203 beyond the injection position.

Although not shown in the figures, the device comprises a latching mechanism to latch the collar 203 relative to the housing at or just prior to the syringe body bottoming out within the device. This latching mechanism is configured to prevent axial movement of the collar back up the housing towards the cap 204. The latching mechanism could comprise, for example, spring fingers formed on one of the collar and the housing and a shoulder on the other of the collar and the housing for flexing past the spring fingers and snapping in place behind them.

When or just before the collar 203 reaches the stop, the projection 209 is no longer prevented from rotating by the rib 210. Therefore the projection 209 is free to travel along the track 208, and the plunger 205 starts to move through the collar 203 under the force of the delivery spring. As already noted, at the stage the collar 203 is prevented from any rearward axial movement within the device.

It will be appreciated that, upon release of the delivery spring, the end of the plunger 202 is not yet in contact with the bung within the syringe body 202. The gap between the plunger head and the bung will vary as noted above. Downward movement of the plunger 205 through the collar 203 is not at this stage entirely uninhibited. As will be clear from the Figures, this motion is restricted by movement of the projection 209 (on the plunger 205) within the track 208. Whilst the collar 203 moves axially with the plunger 205 at this stage, the plunger 205 is also free to move rotationally with respect to the collar 203. The track 208 causes the plunger 205 to alternate its direction of rotation as it moves down the collar 203. It is found that this configuration tends to brake the axial velocity of the plunger 205 as it travels, particularly at each transition, thereby leading to a relatively low velocity of the plunger 205 when it contacts the bung in the syringe body 202. The axial extent of the zig-zag portion of the track 208 is such that it is greater than the maximum likely gap between the plunger head and the bung (following assembly).

After the plunger head contacts the bung, the plunger will continue to move downward at a much reduced speed until the projection 209 exits the zig-zag section of the track 208, whereupon the full force of the delivery spring is exerted on the bung via the plunger.

It will be appreciated that the precise shape of the track can be adjusted depending upon the application requirements. More or fewer direction changes may be employed and the angle of the track may be adjusted. The linear section of track may also be varied in shape and direction depending upon the operating requirements. For example, if a reduced delivery force is required, e.g. the medicament has a very low viscosity, the linear section may be slightly angled relative to the axial direction.

A further advantage of the zig-zag nature of the track 208 is that it occupies a reduced angular space as compared to the cam surface of the prior art. This reduces the extent of the angular rotation that the plunger 205 must undergo, increasing the space available within the device to accommodate other components and/or operations.

It will be appreciated by the person of skill in the art that various modifications may be made to the above described embodiment without departing from the scope of the invention. For example, whilst in the embodiment described above the collar is prevented from rotating relative to the housing and the plunger is able to rotate (following its release), the opposite may be true, i.e. the plunger is prevented from rotating whilst the collar is free to rotate. The locations of the projection 209 and the track 208 may also be reversed, with the track provided on the plunger and the projection provided on the collar. Various other mechanisms for providing relative axial and alternating rotational movement of the plunger and the collar will also be readily apparent.

The invention claimed is:

1. An injection device for delivering a medicament from a syringe contained, in use, within a housing of the device, the device being configured to move the syringe through the housing to cause insertion of a needle of the syringe into a user's skin and to subsequently move a bung of the syringe through a syringe body to deliver medicament through the needle, the device comprising:
   a plunger for engaging with said bung;
   a collar located around the plunger;
   an insertion spring biasing the collar relative to the rear of the device;
   a delivery spring biasing the plunger relative to the collar;
   a stop feature defining the limit of axial movement of the syringe body through the housing; and
   a collar release mechanism for releasing the collar from the rear of the device to commence insertion and a plunger release mechanism for releasing the plunger from the collar, following insertion, to commence delivery of the medicament,
   wherein, following release of the plunger from the collar, the plunger is configured to move axially and rotationally relative to the collar prior to the plunger engaging with the bung, the direction of rotation being changed one or more times with axial movement of the plunger.

2. An injection device according to claim 1, wherein one of said plunger and said collar defines a track and the other comprises a track follower for engaging said track to thereby define the axial and rotational movement of the plunger within the collar.

3. An injection device according to claim 2, wherein said track follower comprises a projection extending radially outwardly from said plunger and said track is formed through, or on an inner surface of, said collar.

4. An injection device according to claim 2, wherein said track comprises two or more sequential and alternately inclined track sections.

5. An injection device according to claim 4, wherein said track comprises a linear track section, subsequent to the inclined sections, which follows only a linear, axial direction.

6. An injection device according to claim 5, wherein the device is configured such that the track follower enters the linear section of the track after the plunger has engaged with the bung.

7. An injection device according to claim 1, wherein said plunger release mechanism comprises a latching mechanism for latching the collar relative to the housing upon or immediately prior to releasing the plunger from the collar.

8. An injection device according to claim 1, wherein the insertion spring and the delivery spring are the same spring.

9. An injection device according to claim 1, further comprising a syringe.

* * * * *